United States Patent [19]
Kassal

[11] Patent Number: 5,595,188
[45] Date of Patent: Jan. 21, 1997

[54] ASSEMBLY PROCESS FOR POLYMER-BASED ACOUSTIC DIFFERENTIAL-OUTPUT SENSOR

[75] Inventor: James J. Kassal, East Lyme, Conn.

[73] Assignee: Flowscan, Inc., Mill Valley, Calif.

[21] Appl. No.: 507,570

[22] Filed: Jul. 26, 1995

[51] Int. Cl.⁶ ........................................ A61B 8/00
[52] U.S. Cl. ............................................ 128/773
[58] Field of Search ................................ 128/715, 773, 128/774, 721; 310/365, 366; 381/67

[56] References Cited

U.S. PATENT DOCUMENTS 4,908,543  3/1990  Sabet-Peyman ................... 310/366
5,365,937  11/1994  Reeves et al. ...................... 128/715

*Primary Examiner*—George Manuel
*Attorney, Agent, or Firm*—Bachman & LaPointe, P.C.

[57] ABSTRACT

The present invention relates to an acoustic sensor having utility in biomedical applications. The sensor is applied to the skin of a patient and is capable of measuring the flexure of the skin caused by acoustic sounds beneath the skin and converting the skin flexure into electrical signals representative of the acoustic sounds. The sensor is formed from a single piece of piezoelectric material having electrically conductive areas on two spaced apart and opposed surfaces. The electrically conductive areas are electrically connected to electrical contacts or connector pins which may be used to hook up the sensor to a measuring device. A method for forming the sensor is also described.

21 Claims, 4 Drawing Sheets

ASSEMBLY PROCESS FOR POLYMER-BASED ACOUSTIC DIFFERENTIAL-OUTPUT SENSOR

BACKGROUND OF THE INVENTION

The present invention relates to lightweight, flexible, disposable sensors for capturing acoustic sounds, in particular cardiac sounds, and to a method of assembling the sensors.

Acoustic pick-up devices that have been traditionally used for capturing heart sounds have had two distinct disadvantages: (a) they have a poor signal to noise ratio in that they are sensitive to air-borne noise which requires that a special, quiet room be used for procedures involving their use; and (b) they are fairly massive in size and therefore substantially reduce any surface vibrations that they are trying to detect.

Commercially available contact microphones are sometimes used to capture heart sounds because they reduce the pick-up of extraneous sounds. On the negative side however is the fact that they influence the surface vibrations even more than other types of pick-ups.

Many of these devices have an additional disadvantage in that they must be held in place. This can introduce unwanted noise from the unavoidable quivering of muscles and creaking of joints in the user's fingers. Belts could be used to avoid this but many users find them objectionable from a convenience standpoint. Still further, many present sensor devices incur signal losses due to air coupling and non-contaneous conformance with the skin.

Attempts have been made to deal with these problems. In one such attempt, a sensor was developed which employed a biaxially poled polyvinylidene fluoride (PVDF) material, 25 microns thick, coated with aluminum metallization. The aluminum metallization was applied to completely cover both sides and then processed by abrasion to form desired electrode patterns. However, the aluminum had a tendency to react with the conducting transfer adhesive that is used to make internal electrical connections. The reaction by-products caused the electrical contacts to become intermittent so that the sensor failed.

SUMMARY OF THE INVENTION

Accordingly, it is an object of the present invention to provide an improved sensor for monitoring acoustic sounds.

It is a further object of the present invention to provide a sensor as above which has particular utility in monitoring cardiac sounds.

It is yet a further object of the present invention to provide an improved method for forming an acoustic sensor.

The foregoing objects are attained by the acoustic sensor and the method of the present invention.

An acoustic sensor in accordance with the present invention comprises a means for sensing the flexure of a surface, such as the skin of a human patient, with which the sensor is in contact and which flexure is caused by a sound, such as heart sounds, produced beneath the surface. The sensing means has spaced apart first and second portions for sensing the flexure and for converting the sensed flexure into electric signals. The first and second portions are preferably formed by a single piece of piezoelectric material having two spaced apart, opposed surfaces coated with an electrically conductive material, such as an electrically conductive metal ink. A first one of the surfaces is provided with an elongated area of electrically conductive material which extends over the majority of the surface area of the surface. A second one of the surfaces is provided with a plurality of discrete areas, preferably three areas, formed by electrically conductive material surrounded by electrically non-conductive areas. The sensor further has electrical contacts for connecting the sensor to measuring or monitoring equipment. The electrical contacts are connected to the areas formed by the electrically conductive material.

The acoustic sensor of the present invention is preferably formed by providing a piece of piezoelectric material having first and second spaced apart opposed surfaces and electrically conductive areas on each of said surfaces, bonding a strip of reinforcing material to the first surface adjacent a first end of the piece of piezoelectric material so that the reinforcing strip extends along the first surface for a desired distance from the first end, mounting electrical contacts to the second surface of the piezoelectric material so that end portions of the contacts are positioned at a distance from the first end less than the desired distance of the reinforcing strip, providing a substrate material having a width coextensive with the width of the piece of piezoelectric material and a length substantially less than half of the length of the piece of piezoelectric material, and wrapping a first portion of the piece of piezoelectric material containing the first end around one end of the substrate. Thereafter, part of the first portion containing the first end is folded back on itself to expose the electrical contacts. Subsequently, a second portion of the piece of piezoelectric material containing a second end is placed under tension and wrapped around a second end of the substrate. The second end of the piezoelectric material is then placed in contact with the folded back part of the first portion so that it overlaps the first end.

Other details, objects and advantages of the acoustic sensor and the assembly method of the present invention are set forth in the following detailed description and the accompanying drawings wherein like reference numerals depict like elements.

DETAILED DESCRIPTION OF THE PREFERRED EMBODIMENT(S)

Figure 1:
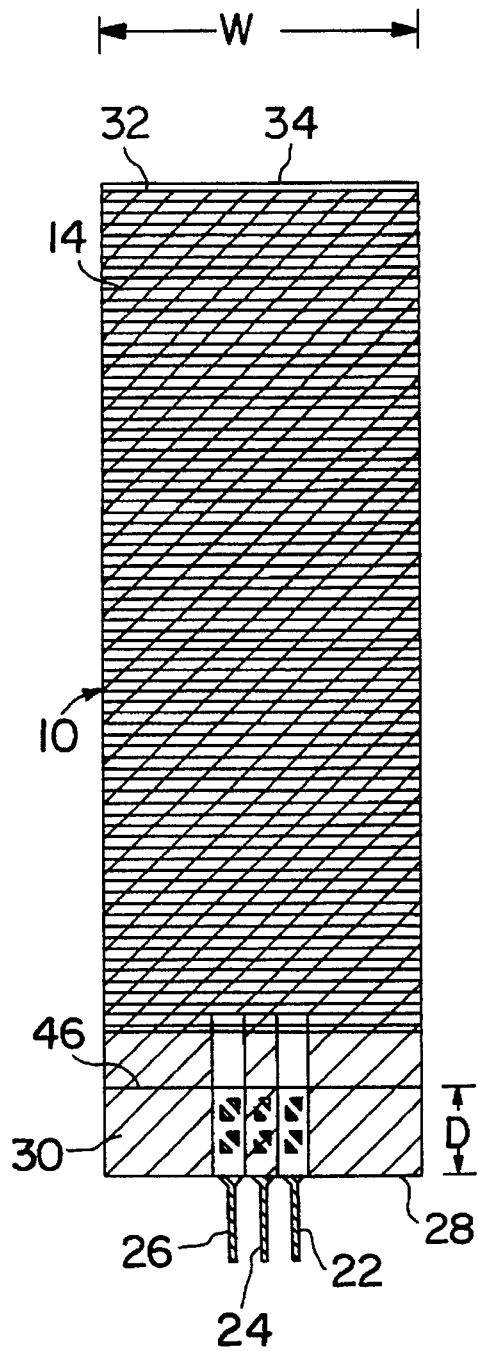
FIG. 1 illustrates a first surface of a piezoelectric element used to form the sensor of the present invention.
Figure 2:
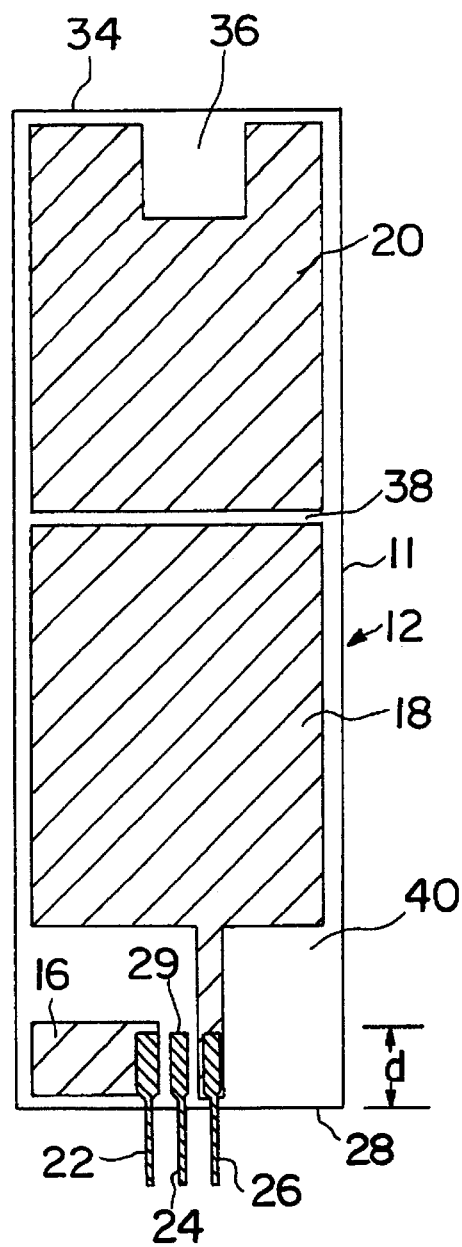
FIG. 2 illustrates a second surface, opposed to the first surface, of the piezoelectric element used to form the sensor of the present invention.

Referring now to the drawings, FIGS. 1 and 2 illustrate the spaced apart upper and lower surfaces 10 and 12 of a piezoelectric material 11, such as polyvinylidene fluoride, from which the acoustic sensor of the present invention is formed. The surfaces 10 and 12 are spaced apart by the thickness of the piezoelectric material. Polyvinylidene fluoride (PVDF) has been found to be a useful material because it is an anisotropic piezoelectric polymer that produces surface charges of equal magnitude and opposite polarity on opposite surfaces when a mechanical strain is imposed on the material. As shown in these figures, and as will be discussed in more detail hereinafter, the piezoelectric material is coated on both sides with areas 14, 16, 18 and 20 of an electrically conductive material. Preferably, the electrically conductive material comprises an electrically conductive, silver elastomeric ink which is silk screened onto the surfaces 10 and 12 of the piezoelectric material in desired patterns.

As shown in FIGS. 1 and 2, the piezoelectric material has three electrical contacts 22, 24 and 26 mounted adjacent to the surface 12 and adjacent to a first end 28 thereof. The electrical contacts each have an end portion 29 which is located at a distance d from the first end 28. The electrical contacts are formed by metal connector pins which have small prongs which penetrate the piezoelectric material and which can be crimped to secure them in place and provide electrical contact with a desired conducting area. The method of attaching the electrical contacts or connector pins to the piezoelectric material is well known in the art and does not form part of the present invention.

As shown in FIG. 2, the electrical contact or connector pin 22 is electrically connected to electrically conductive area 16 and the electrical contact or connector pin 26 is electrically connected to electrically conductive area 18. The remaining electrical contact or connector pin 24 is electrically connected to the electrically conductive area 14 on the upper surface 10. Any suitable means known in the art such as the electrically conductive ink may be used to connect the contacts to the respective areas 14, 16 and 18. The electrically conductive area 20 is not electrically connected to any of the electrical contacts when the piezoelectric material is in its non-folded state.

Prior to the connection of the electrical contacts 22, 24 and 26 to the piezoelectric material, a strip 30 of reinforcing material is bonded to the surface 10 adjacent the first end 28. The reinforcing material extends along the surface 10 a distance D from the first end 28. Preferably, the distance D is greater than the aforementioned distance d. The reinforcing strip 30 insures that the acoustic sensor of the present invention is correctly assembled. It ensures, without any effort, that the length of the piezoelectric material is just right to wrap around a substrate 42 while completely covering the area of the electrical contacts without extending too far.

The reinforcement strip 30 is preferably formed from a stiff plastic such as polyester and preferably has a thickness of about 0.005 inches. The reinforcement strip 30 further has a pressure sensitive adhesive (not shown) applied to the surface that is not bonded to the surface 10.

As shown in FIG. 1, electrically conductive area 14 extends over a majority of the surface area of surface 10. In order to provide a Faraday shield for minimizing the pickup of unwanted electromagnetic signals, the area 14 has a width which corresponds to the width W of the piezoelectric material. There is a portion 32 of the surface 10 adjacent a second end 34 of the piezoelectric material where there is no electrically conductive metal material. This portion 32 is present to prevent short circuits when the piezoelectric material is finally assembled into the acoustic sensor.

Referring now to FIG. 2, each of the electrically conductive areas 16, 18 and 20 formed on the surface 12 are separated by electrically non-conductive portions and are spaced from the edges of the piezoelectric material. These electrically non-conductive portions are provided to prevent short circuits when the piezoelectric material is finally assembled into the acoustic sensor and to maximize the effectiveness of conducting area 14 (FIG. 2) as a Faraday shield. Additionally, certain of the electrically non-conductive areas such as area 38 forms a fold line which is used during the assembly of the sensor. An electrically non-conductive notch area 36 is provided adjacent the second end 34. The notch area 36 is dimensioned so that the electrically conductive material forming area 20 does not contact either electrical contact 24 or 26 when the acoustic sensor is assembled.

Preferably, the combined surface area of areas 18 and 20 is substantially equal to the surface area of area 14 so that when the capacitance of the assembled acoustic sensor is measured between pins 24 and 26, the result is substantially equal to the capacitance measured between pins 22 and 24. This helps maintain the electrical balance between the signals that are developed at pins 22 and 26 during use.

A pigmented, elastomeric, conformal coating 27 (see FIG. 4) may be applied over the area 14. Preferably, this coating does not extend within 0.20 inches of the reinforcement strip 30. The coating 27 helps to cover the exposed surface area of the final acoustic sensor assembly and eliminates any need to apply a protective coating after the sensor is assembled.

Figure 3:
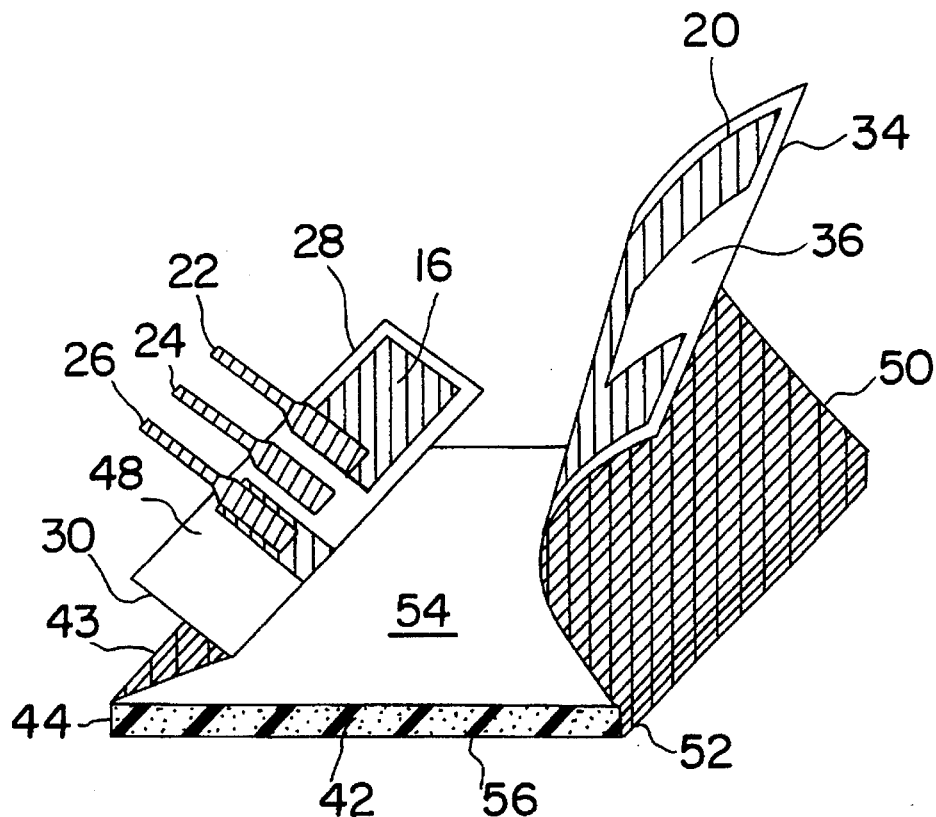
FIG. 3 illustrates the manner in which a sensor in accordance with the present invention is assembled.

Referring now to FIG. 3, the method for assembling the acoustic sensor will now be discussed. First, a substrate 42 is provided having a width substantially equal to the width W of the piezoelectric material and a length less than one-half of the length of the piezoelectric material. The substrate 42 may have any desired thickness, preferably about 0.030 inches. The substrate 42 may be formed from a flexible material such as dense neoprene rubber foam or solid rubber. Preferably, the substrate has a high strength, pressure sensitive adhesive pre-applied to its upper and lower surfaces 54 and 56 to facilitate assembly. One of the advantages to using a material such as dense neoprene rubber foam is that very little force is required to bend it.

The substrate 42 is then placed on the surface 12 of the piezoelectric material so that the bottom surface 56 of the substrate contacts the electrically conductive area 18. The adhesive present on the bottom surface 56 of the substrate will cause the piezoelectric material to adhere to the substrate. Thereafter, a first portion 43 of the piezoelectric material containing the first end 28 is wrapped over a first end 44 of the substrate. Before portion 43 of the piezoelectric material is bonded to the upper surface 54 of the substrate 42, a part 48 of the first portion containing electrical contacts 22, 24 and 26 and the reinforcement strip 30 is folded back onto a portion of the surface 10. A transverse edge 46 of the reinforcement strip is used as a first fold line and therefore determines the extent of the part 48 to be folded back. After this folding step, the portion 43 is pressed against the upper surface of the substrate and the folded pack portion 48 is pressed against that part of the surface 10 of the portion 43 so that electrically conductive area 16 is facing outwardly. The folded back portion 48 is maintained in this position by the adhesive material applied to the reinforcement strip 30.

Subsequently, a second portion 50 of the piezoelectric material containing electrically conductive area 20, notch area 36 and second end 34 is placed under tension and wrapped around a second end 52 of the substrate 42. Preferably, fold line 38 is positioned adjacent the end 52. Prior to bonding the second portion 50 to the upper surface 54 of the substrate, a strip (not shown) of electrically conductive adhesive material is applied across the electrical contacts 22, 24 and 26 and the electrically conductive area 16. The adhesive material, due to its ability to conduct electricity, should not interfere in any way with the electrical conductivity of the area 16. If desired, the strip of adhesive material may be applied before the assembly operation begins and covered by a removable protective liner (not shown).

Figure 4:
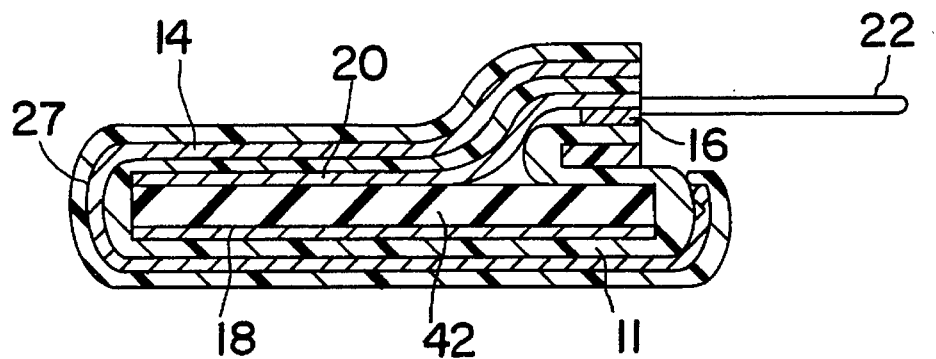
FIG. 4 is a sectional view of a sensor in accordance with the present invention.

The second portion 50, while under tension, is then pressed against the uncovered portion of the upper surface 54 of the substrate 42 and against the folded back portion 48. In the final assembly, the second end 34 and the first end 28 of the piezoelectric material preferably overlap one another and form a smooth edge. Additionally, area 20 is in electrical contact with area 16 and the notch area 36 is disposed over portions of contact pins 24 and 26. The surface 10 of the piezoelectric material with the conformal coating 27 thereon forms the outer surfaces of the sensor. FIG. 4 illustrates a sectional view of the finally assembled sensor.

The acoustic sensors of the present invention have particular utility in the measurement of heart sounds. This is because the sensors are capable of flexing with the skin. This flexure produces a dynamic tensile strain in the piezoelectric sensing portions of the sensor formed by the areas 14, 16, 18 and 20, which strains result in the production of two electrical signals (voltage) analogous to the flexure generated by the acoustic sensor.

Figure 5:
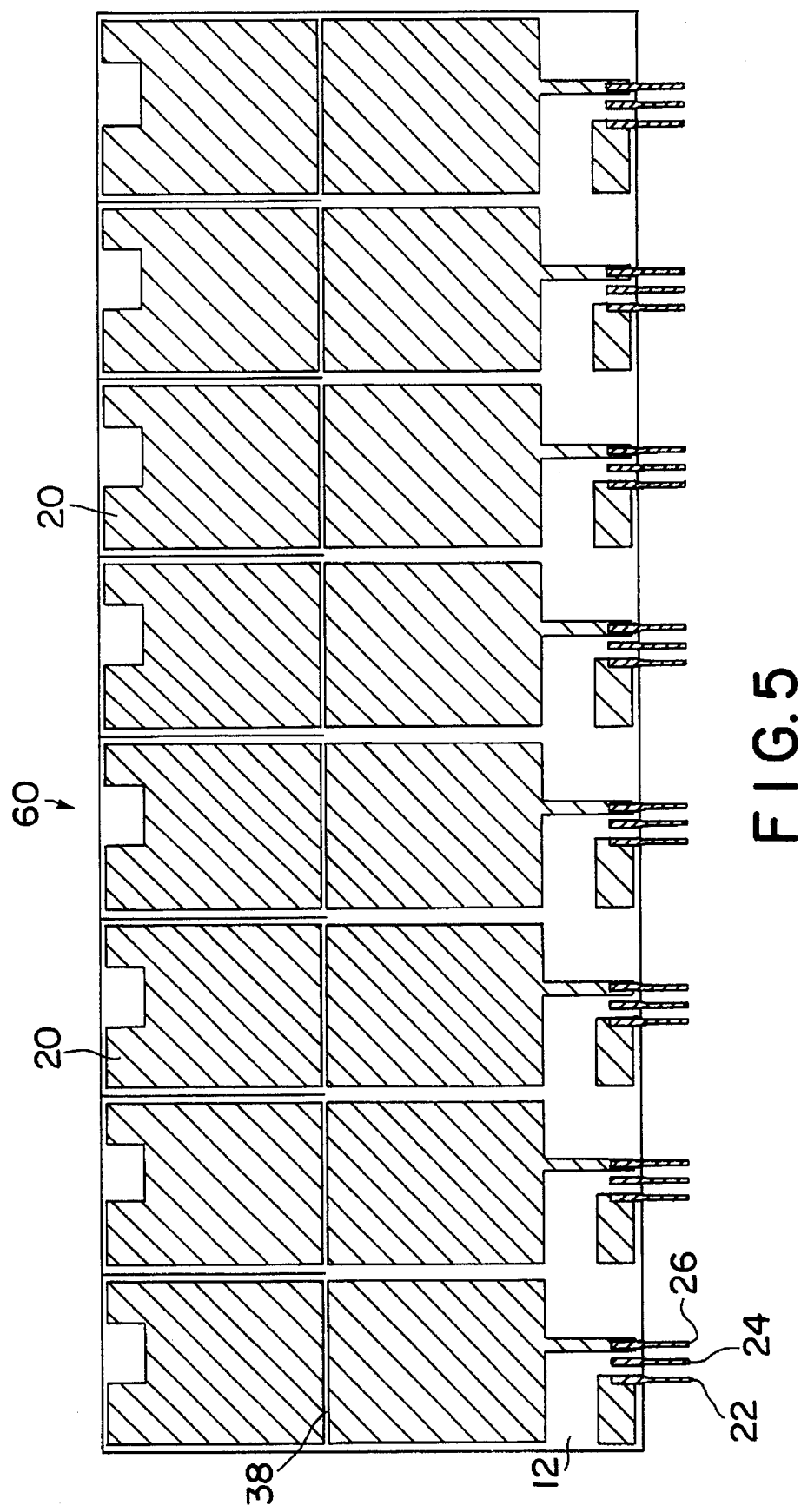
FIG. 5 illustrates a sheet of piezoelectric material from which a plurality of sensors in accordance with the present invention may be formed.

While the acoustic sensor of the present invention and its method of assembly have been described in the context of a single piece of piezoelectric material and a single sensor, it should be recognized that a plurality of sensors could be formed at one time using a sheet of piezoelectric material having sufficient material to form more than one sensor. FIG. 5 illustrates the bottom surface of such a sheet 60 of material. The number of sensors per sheet is limited only by dimensional limitations of the raw piezoelectric material sheet stock. The substrate material used to form the sensors may be pre-cut into strips having a length equal to the number of elements on the piezoelectric material sheet times the width of each sensor.

When a sheet 60 of piezoelectric material is used to form the sensors, that portion of the sheet containing areas 20 should be pre-split. This is important because each fold line 38 must be formed individually to ensure that (1) entrapped air is avoided in the bonded interface between the substrate and the surface 12; (2) the forward-most portion of the piezoelectric material with area 20 can be forced to conform to the irregular surface formed by the electrical contacts or connector pins 22, 24, and 26; and (3) the proper amount of tension is applied to each area 20 as it is laminated to the substrate.

After all folding operations are completed, all of the sensors thus formed are physically joined together and must subsequently be cut into individual sensors.

Figure 6:
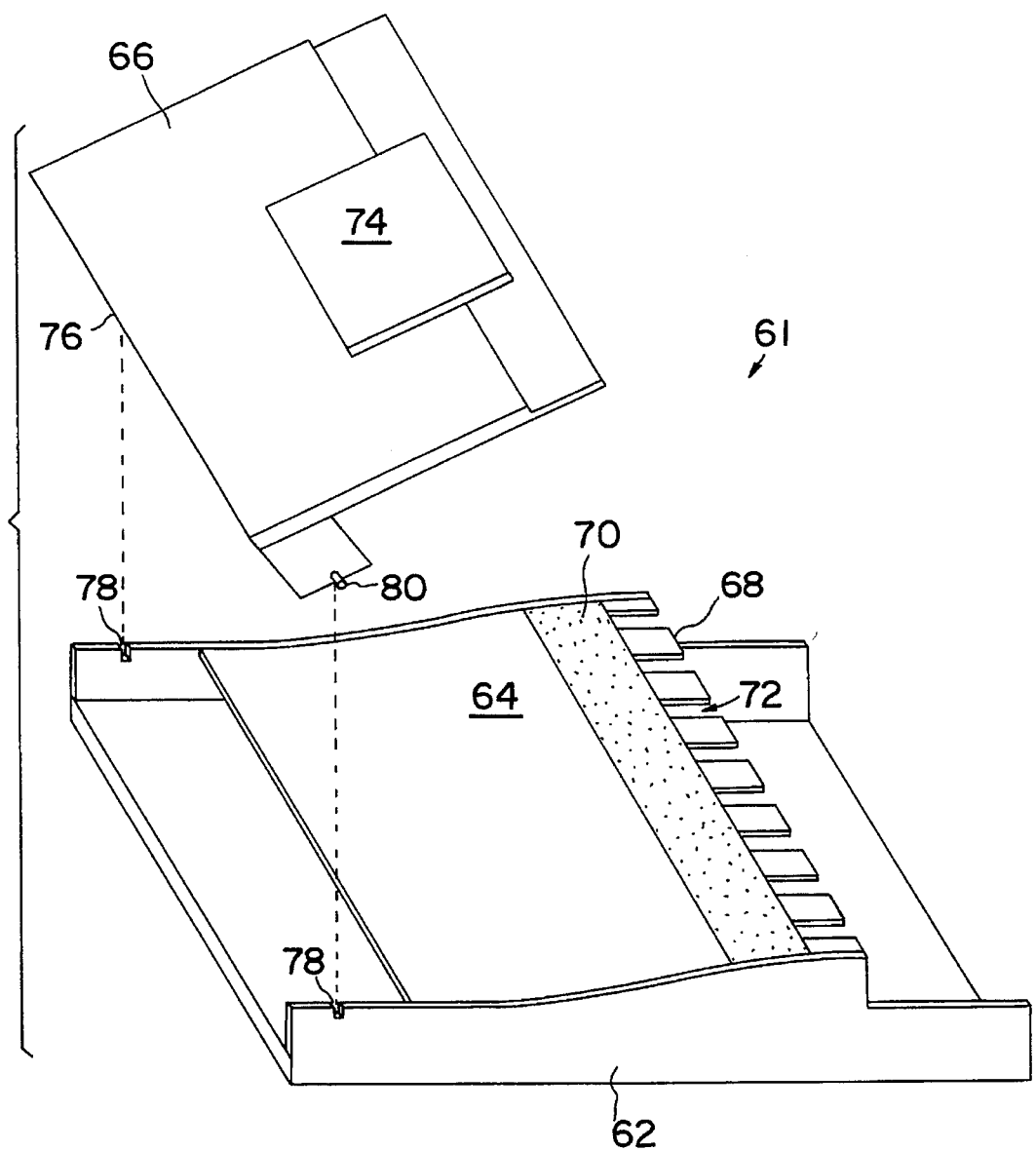
FIG. 6 is an exploded view of a tool used to perform the method of the present invention.

Assembly of the sensors from sheet 60 may be carried out using a tool 61 specific for that purpose. FIG. 6 illustrates the tool. As shown in this figure, the tool consists of two, separable parts: (1) a base 62 with a curved work surface 64 which helps ensure that both the top and the bottom layers of the folded piezoelectric material will have some residual tension after assembly is complete; and (2) a swing-down arm 66 that precisely positions the substrate on the sheet of piezoelectric material. The swing arm 66 has a pair of pins 80 which fit into slots 78 so as to form a mechanism about which the arm 66 can pivot relative to the base 62. When using the tool 61, the first fold and the associated bonding of the portion 48 to the surface 10 is accomplished prior to mounting the sheet 60 of sensor elements on the curved work surface 64.

The work surface of the tool preferably has an elevated forward edge 68 that determines where the folded piezoelectric sensor elements must be placed. The folded piezoelectric sensor elements are placed connector side down onto the work surface 64 with the folded edge flush with the forward edge 68 of the work surface. This ensures that the piezoelectric material is squarely positioned where the swing arm can properly place the substrate. A low tack, temporary adhesive 70 applied to the work surface holds the piezoelectric material in place on the fixture during the assembly process. Notches 72 in the forward portion of the work surface 64 allow the electrical contacts or connector pins 22, 24, 26 to be recessed and not form bulges in the piezoelectric material.

The substrate 42 is mounted in the swing arm which has a retainer 74 for the substrate and guide surfaces to precisely control its orientation. A bottom liner (not shown) applied to the substrate 42 is partially removed and folded back onto itself so that when the exposed pressure sensitive adhesive of the substrate 42 makes contact with the piezoelectric material 11, only a narrow strip of the pressure sensitive adhesive makes initial contact with the piezoelectric material sheet. At this time, the rear portion 76 of the swing arm 66 is lifted so that the pins 80 separate from the slots 78 and then pulled to separate it from the substrate 42. The liner is then completely removed and the substrate 42 is pressed from the forward edge to the back onto the piezoelectric material sheet 11 in a manner that avoids entrapped air in the bonded interface between the piezoelectric material 11 and the substrate 42. Thereafter, a top liner (not shown) is removed from the substrate strip. The connector pins or electrical contacts 22, 24, 26 are folded up onto the substrate 42 while ensuring that fold line 40 is tight against the end 44 of the substrate 42. At this point, the forward edge of the piezoelectric material directly beneath the connector pins is flush with the forward edge of the substrate. A single strip of electrically conductive transfer adhesive is applied with the forward edge flush with the forward edge of the assembly. After pressing it firmly onto the assembly, the protective liner is lifted and discarded. Each area 20 is then tensioned gently by hand and simultaneously smoothed onto the substrate to avoid entrapped air.

Once assembled, the multiple sensors may be electrically connected to a test fixture that verifies the proper electrical function of each sensor. The sensor assembly is then cut into individual sensors ready for final testing and packaging.

Sensors formed in accordance with the present invention are lightweight, flexible and disposable. They have particular utility in converting cardiac sounds to analogous electrical signals with a minimum of interference from sounds originating outside the patient. Due to their flexibility, the sensors are compliant and conform to the contour(s) of the surface to which they are attached. The sensors of the present invention may be used with any phonocardiographic equipment.

The sensors may be applied to a patient using adhesive patches (not shown) which provide good adhesion and acoustic coupling but do not hurt to remove. The patches further prevent contact between the electrical contacts 22, 24 and 26 and any gel applied to the skin of the patient.

Each sensor manufactured in accordance with the present invention may be used up to 12 times.

While the acoustic sensors of the present invention have particular utility in biomedical applications, they could also be used in mechanical applications.

It is apparent that there has been provided in accordance with this invention an acoustic sensor and a method for manufacturing an acoustic sensor which fully satisfies the objects, means and advantages set forth hereinbefore. While the invention has been described in combination with specific embodiments thereof, it is evident that many alternatives, modifications, and variations will be apparent to those skilled in the art in light of the foregoing description. Accordingly, it is intended to embrace all such alternatives, modifications and variations as fall within the spirit and broad scope of the appended claims.

What is claimed is:

1. An acoustic sensor for detecting sounds and converting the sounds to analogous electrical signals comprising:

means for sensing flexure of a surface with which said sensor is in contact and which flexure is caused by sounds produced beneath said surface;

said sensing means including spaced apart first and second portions for sensing said flexure and for converting said sensed flexure into said electrical signals;

said first and second sensing portions being formed by a single piece of piezoelectric material having two spaced apart, opposed surfaces coated in selected areas with an electrically conductive material;

a first one of said two opposed surfaces having one elongated area of said electrically conductive material; and a second one of said two opposed surfaces having a plurality of discrete areas of said electrically conductive material, said plurality of discrete areas being spaced along said second one of said two opposed surfaces in a longitudinal direction.

2. The acoustic sensor of claim 1 further comprising:

said second one of said two opposed surfaces having electrically non-conductive areas surrounding said discrete areas of electrically conductive material.

3. The acoustic sensor of claim 1 further comprising:

said piezoelectric material having a width; and said electrically conductive area on said first one of said two opposed surfaces having a width equal to the width of said piezoelectric material so as to form a Faraday shield for minimizing any pickup of unwanted electromagnetic signals.

4. The acoustic sensor of claim 1 further comprising:

a substrate formed from a flexible material; and said substrate being in contact with said second one of said two opposed surfaces when said piezoelectric material is folded around said substrate.

5. The acoustic sensor of claim 4 wherein said substrate is formed by a neoprene rubber foam material having a high strength, pressure sensitive adhesive material on two opposed surfaces, which surfaces are to be contacted by said piezoelectric material.

6. The acoustic sensor of claim 1 further comprising:

said piezoelectric material being a sheet of polyvinylidene fluoride; and said electrically conductive material comprising an electrically conductive silver elastomeric ink.

7. The acoustic sensor of claim 1 further comprising:

an elastomeric, conformal coating applied to said first one of said two opposed surfaces to protect said sensor.

8. An acoustic sensor for detecting sounds and converting the sounds to analogous electrical signals comprising:

means for sensing flexure of a surface with which said sensor is in contact and which flexure is caused by sounds produced beneath said surface;

said sensing means including spaced apart first and second portions for sensing said flexure and for converting said sensed flexure into said electrical signals;

said first and second sensing portions being formed by a single piece of piezoelectric material having two spaced apart, opposed surfaces coated in selected areas with an electrically conductive material;

a first one of said two opposed surfaces having one elongated area of said electrically conductive material;

a second one of said two opposed surfaces having a plurality of discrete areas of said electrically conductive material;

a plurality of electrical contacts mounted to said piezoelectric material;

a reinforcement strip attached to a portion of said first one of said two opposed surfaces; and said reinforcement strip being positioned in an overlapping relationship with said electrical contacts and forming a first fold line for said piezoelectric material.

9. The acoustic sensor of claim 8 further comprising:

said second one of said two opposed surfaces having three discrete areas of said electrically conductive material;

two of said discrete areas being electrically connected to two of said plurality of electrical contacts; and a third of said discrete areas being electrically unconnected to any of said electrical contacts.

10. The acoustic sensor of claim 9 wherein said electrically conductive area on said first one of said two opposed surfaces is electronically connected to a third electrical contact.

11. The acoustic sensor of claim 10 wherein said second one of said two opposed surfaces has an electrically non-conductive area which overlaps two of said plurality of electrical contacts when said piezoelectric material is folded on itself.

12. An acoustic sensor for detecting sounds and converting the sounds to analogous electrical signals comprising:

means for sensing flexure of a surface with which said sensor is in contact and which flexure is caused by sounds produced beneath said surface;

said sensing means including spaced apart first and second portions for sensing said flexure and for converting said sensed flexure into said electrical signals;

said first and second sensing portions being formed by a single piece of piezoelectric material having two spaced apart, opposed surfaces coated in selected areas with an electrically conductive material;

a first one of said two opposed surfaces having one elongated area of said electrically conductive material;

a second one of said two opposed surfaces having a plurality of discrete areas of said electrically conductive material;

a flexible substrate material;

said one elongated area on said first one of said two opposed surfaces having a desired area and being electrically connected to a first electrical contact;

said second one of said two opposed surfaces having a first electrically conductive area connected to a second electrical contact, a second electrically conductive area electrically connected to a third electrical contact, and a third electrically conductive area which contacts said second electrically conductive area when said piezoelectric material is wrapped around said substrate material; and said combined area of said first and third electrically conductive areas being substantially equal to the area of said elongated area so that a capacitance measured between said first and second electrical contacts is substantially equal to a capacitance measured between the first and third electrical contacts.

13. A method for assembling an acoustic sensor comprising the steps of:

providing a piece of piezoelectric material having first and second spaced apart opposed surfaces with electrically conductive areas on said surfaces, said piezoelectric material having a width and a length;

providing a substrate material having a width substantially equal to the width of said piezoelectric material, a length less than half of the length of said piece of piezoelectric material, and an adhesive applied to two of its surfaces;

placing said substrate material upon said first surface of said piezoelectric material so that there are first and second portions of said piezoelectric material extending beyond said substrate material;

wrapping said first portion of said piezoelectric material around a first end of said substrate material and wrapping said second portion of said piezoelectric material around a second end of said substrate material until said second portion overlaps said first portion.

14. A method for assembling an acoustic sensor comprising the steps of:

providing a piece of piezoelectric material having first and second spaced apart opposed surfaces with electrically conductive areas on said surfaces, said piezoelectric material having a width and a length;

providing a substrate material having a width substantially equal to the width of said piezoelectric material, a length less than half of the length of said piece of piezoelectric material, and an adhesive applied to two of its surfaces;

placing said substrate material upon said first surface of said piezoelectric material so that there are first and second portions of said piezoelectric material extending beyond said substrate material;

wrapping said first portion of said piezoelectric material around a first end of said substrate material and wrapping said second portion of said piezoelectric material around a second end of said substrate material until said second portion overlaps said first portion;

bonding a strip of reinforcing material to said first surface of said piezoelectric material adjacent a first end of said piezoelectric material so that said strip of reinforcing material extends along said first surface a desired distance from said first end and forms part of said first portion;

mounting electrical contacts to said piezoelectric material so that said electrical contacts abut said second surface of said piezoelectric material and have end portions positioned from said first end by a distance shorter than said desired distance; and performing said bonding and mounting steps prior to said placing step.

15. The method of claim 14 further comprising the step of:

applying an adhesive material to a surface of said reinforcing strip not in contact with said first surface of said piezoelectric material.

16. The method of claim 15 wherein said wrapping step comprises:

folding part of said first portion containing said reinforcing strip and said electrical contacts back on itself using an edge of said reinforcing strip as a fold line;

bonding said folded part to said second surface of said piezoelectric material; and pressing said first portion with said folded part against said substrate material to cause part of said second surface of said piezoelectric material to adhere against said substrate material.

17. The method of claim 16 wherein said wrapping step further comprises:

applying an adhesive material to said second surface of said piezoelectric material in the vicinity of said electrical contacts;

tensioning said second portion of said piezoelectric material; and pressing a first part of said second portion against a surface of said substrate material so as to adhere said first part to said substrate material and pressing a second part of said second portion against said adhesive material on said second surface of said piezoelectric material so that said second portion overlaps said first portion.

18. The method of claim 14 wherein said piezoelectric material providing step comprises providing a piezoelectric material having a conformal coating applied to portions of said first surface.

19. The method of claim 14 further comprising:

forming an elongated electrically conductive area on said first surface and three discrete electrically conductive areas on said second surface prior to said bonding and mounting steps.

20. The method of claim 19 wherein said mounting step further comprises:

placing a first one of said electrical contacts in electrical contact with a first one of said discrete areas on said second surface;

placing a second one of said electrical contacts in electrical contact with a second one of said discrete areas on said second surface; and placing a third one of said electrical contacts in electrical contact with said elongated area on said first surface.

21. The method of claim 20 wherein:

said forming step also comprises forming an electrically non-conductive notch area on said second surface adjacent said second end; and said wrapping step comprises wrapping said second portion around said substrate material so that said notch area overlaps two of said electrical contacts and so that said first discrete area is in contact with a third discrete area of electrically conductive material on said second surface.

* * * * *